US009779299B2

(12) United States Patent
Strombom et al.

(10) Patent No.: US 9,779,299 B2
(45) Date of Patent: *Oct. 3, 2017

(54) METHOD FOR DISPLAYING GAZE POINT DATA BASED ON AN EYE-TRACKING UNIT

(71) Applicant: TOBII AB, Danderyd (SE)

(72) Inventors: Johan Strombom, Sollentuna (SE); Marten Skogo, Danderyd (SE); Per Nystedt, Akersberga (SE); Simon Gustafsson, Taby (SE); John Mikael Holtz Elvesjo, Stockholm (SE); Peter Blixt, Hagersten (SE)

(73) Assignee: TOBII AB, Danderyd (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/153,267

(22) Filed: Jan. 13, 2014

(65) Prior Publication Data

US 2014/0146156 A1    May 29, 2014

Related U.S. Application Data

(63) Continuation of application No. 13/145,636, filed as application No. PCT/EP2009/000480 on Jan. 26, 2009, now Pat. No. 9,495,589.

(51) Int. Cl.
*A61B 3/113* (2006.01)
*G06K 9/00* (2006.01)
*H04N 7/18* (2006.01)

(52) U.S. Cl.
CPC .......... *G06K 9/00604* (2013.01); *A61B 3/113* (2013.01); *H04N 7/18* (2013.01)

(58) Field of Classification Search
CPC ................................ G06K 9/00; G06K 9/00604
See application file for complete search history.

(56) References Cited

U.S. PATENT DOCUMENTS 4,896,962 A * 1/1990 Menn ...................... F41G 3/225
250/203.3
4,967,268 A * 10/1990 Lipton ............... H04N 13/0438
348/521
4,973,149 A * 11/1990 Hutchinson ............ A61B 3/113
351/210
5,325,192 A * 6/1994 Allen ................ H04N 13/0497
348/164

(Continued)

FOREIGN PATENT DOCUMENTS

EP 0125808 4/1984
JP 2003-225207 8/2003

(Continued)

OTHER PUBLICATIONS

U.S. Appl. No. 13/145,636 Notice of Allowance dated July 21, 2016.

*Primary Examiner* — Richard Torrente
*Assistant Examiner* — Irfan Habib
(74) *Attorney, Agent, or Firm* — Kilpatrick Townsend & Stockton LLP

(57) ABSTRACT

A method of presenting gaze-point data of a subject detected by an eye-tracking unit includes presenting a test scene picture acquired by a camera unit, and displaying shapes on the test scene picture. The shapes represent momentary gaze points of the subject.

7 Claims, 14 Drawing Sheets

(56) References Cited

U.S. PATENT DOCUMENTS

| | | | | |
|---|---|---|---|---|
| 5,689,619 A * | 11/1997 | Smyth | G02B 27/0093 | 345/156 |
| 6,243,076 B1 * | 6/2001 | Hatfield | G06F 3/013 | 345/156 |
| 6,307,521 B1 * | 10/2001 | Schindler | G01S 13/86 | 342/53 |
| 6,351,273 B1 * | 2/2002 | Lemelson | G06F 3/0485 | 704/271 |
| 6,373,961 B1 * | 4/2002 | Richardson | G06F 3/013 | 345/8 |
| 6,381,339 B1 * | 4/2002 | Brown et al. | G06F 3/013 | 382/100 |
| 6,637,883 B1 | 10/2003 | Tengshe et al. | | |
| 7,246,904 B2 * | 7/2007 | Knaan | A61B 3/113 | 351/206 |
| 7,266,995 B2 * | 9/2007 | Skogo | G01N 13/02 | 73/64.48 |
| 7,391,887 B2 * | 6/2008 | Durnell | G06T 7/73 | 340/5.8 |
| 7,438,414 B2 * | 10/2008 | Rosenberg | G06F 3/013 | 351/209 |
| 7,538,744 B1 * | 5/2009 | Liu | G06F 3/013 | 345/7 |
| 7,542,210 B2 * | 6/2009 | Chirieleison, Sr. | G02B 27/0093 | 345/8 |
| 7,572,008 B2 * | 8/2009 | Elvesjo | G06K 9/00604 | 351/206 |
| 7,720,264 B2 * | 5/2010 | Fouquet | G01J 3/26 | 382/103 |
| 7,736,000 B2 * | 6/2010 | Enriquez | A61B 3/113 | 351/205 |
| 7,747,068 B1 * | 6/2010 | Smyth | G03B 17/00 | 382/154 |
| 7,810,926 B2 * | 10/2010 | Connell, II | A61B 3/111 | 351/204 |
| 7,883,415 B2 * | 2/2011 | Larsen | A63F 13/10 | 345/7 |
| 7,889,244 B2 * | 2/2011 | Tsukizawa | G06F 3/012 | 348/222.1 |
| 7,963,652 B2 * | 6/2011 | Vertegaal | G06K 9/00604 | 351/205 |
| 8,025,400 B2 * | 9/2011 | Chernyak | A61B 3/11 | 351/205 |
| 8,032,842 B2 * | 10/2011 | Kwon | G06K 9/00604 | 351/209 |
| 8,126,208 B2 * | 2/2012 | Steinberg | H04N 5/23212 | 382/103 |
| 8,136,944 B2 * | 3/2012 | De Lemos | A61B 3/113 | 351/209 |
| 8,180,101 B2 * | 5/2012 | Sun | G01B 11/2504 | 348/180 |
| 8,185,845 B2 * | 5/2012 | Bjorklund | G06F 3/013 | 345/158 |
| 8,274,578 B2 * | 9/2012 | Hong | G06F 3/013 | 348/222.1 |
| 8,339,446 B2 * | 12/2012 | Blixt | A61B 3/113 | 348/78 |
| 8,457,352 B2 * | 6/2013 | Hennessey | A61B 3/113 | 382/103 |
| 8,464,165 B2 * | 6/2013 | Van Os | G09G 3/003 | 345/419 |
| 8,467,133 B2 * | 6/2013 | Miller | G02B 27/017 | 353/28 |
| 8,487,838 B2 * | 7/2013 | Lewis | A61B 3/113 | 345/8 |
| 8,500,278 B2 * | 8/2013 | Lo | A61B 3/024 | 351/206 |
| 8,500,281 B2 * | 8/2013 | Ahn | A61B 3/113 | 351/209 |
| 8,553,936 B2 * | 10/2013 | Fogt | A63B 69/0002 | 382/103 |
| 8,860,660 B2 * | 10/2014 | Jahnke | G06F 3/013 | 345/156 |
| 8,878,773 B1 * | 11/2014 | Bozarth | G06K 9/00604 | 345/156 |
| 8,879,801 B2 * | 11/2014 | Ragland | G06F 3/011 | 351/209 |
| 8,885,877 B2 * | 11/2014 | Publicover | G06K 9/00604 | 382/103 |
| 8,885,882 B1 * | 11/2014 | Yin | G06F 3/00 | 382/103 |
| 8,911,087 B2 * | 12/2014 | Publicover | A61B 3/113 | 351/200 |
| 8,929,589 B2 * | 1/2015 | Publicover | G06K 9/00604 | 382/103 |
| 8,955,973 B2 * | 2/2015 | Raffle | A61B 3/113 | 351/209 |
| 9,039,179 B2 * | 5/2015 | Brown, Jr. | A61B 3/113 | 351/208 |
| 9,179,833 B2 * | 11/2015 | Narasimha-Iyer | A61B 3/0091 | |
| 9,179,838 B2 * | 11/2015 | Skogo | A61B 3/113 | |
| 9,329,684 B2 * | 5/2016 | Horesh | G06F 3/013 | |
| 9,330,302 B2 * | 5/2016 | Thukral | G06K 9/00335 | |
| 9,345,402 B2 * | 5/2016 | Gao | A61B 3/113 | |
| 9,355,315 B2 * | 5/2016 | Vugdelija | G06K 9/6218 | |
| 9,361,833 B2 * | 6/2016 | Kamhi | G06K 9/00604 | |
| 9,386,921 B2 * | 7/2016 | Cleveland | G03B 9/02 | |
| 9,398,848 B2 * | 7/2016 | Hansen | A61B 3/113 | |
| 9,430,040 B2 * | 8/2016 | Zhang | G06F 3/013 | |
| 9,442,644 B1 * | 9/2016 | Bostick | G06F 3/04842 | |
| 9,468,373 B2 * | 10/2016 | Larsen | G06K 9/00604 | |
| 9,480,397 B2 * | 11/2016 | Larsen | G06K 9/00604 | |
| 9,503,713 B2 * | 11/2016 | Fuka | A61B 3/0058 | |
| 9,552,061 B2 * | 1/2017 | Zhang | G06T 7/0002 | |
| 9,619,707 B2 * | 4/2017 | Sakamaki | G06K 9/00604 | |
| 9,639,154 B2 * | 5/2017 | Bostick | G06F 3/013 | |
| 9,639,745 B2 * | 5/2017 | Williams | G06K 9/00335 | |
| 9,646,207 B2 * | 5/2017 | Kuldkepp | G06K 9/00604 | |
| 2002/0105482 A1 * | 8/2002 | Lemelson | G06F 3/0485 | 345/7 |
| 2002/0167462 A1 * | 11/2002 | Lewis | G02B 27/0093 | 345/7 |
| 2004/0170304 A1 * | 9/2004 | Haven | A61B 3/113 | 382/115 |
| 2004/0174496 A1 * | 9/2004 | Ji | G06F 3/013 | 351/209 |
| 2005/0175218 A1 * | 8/2005 | Vertegaal | A61B 3/113 | 382/103 |
| 2005/0190180 A1 * | 9/2005 | Jin | H04N 13/0018 | 345/419 |
| 2006/0028400 A1 * | 2/2006 | Lapstun | G02B 26/06 | 345/8 |
| 2006/0149426 A1 * | 7/2006 | Unkrich | B60R 25/255 | 701/1 |
| 2009/0174864 A1 * | 7/2009 | Hutchin | A61B 3/113 | 351/210 |
| 2009/0219386 A1 * | 9/2009 | Ebisawa | A61B 3/11 | 348/78 |
| 2009/0237327 A1 * | 9/2009 | Park | G02B 27/2264 | 345/8 |
| 2010/0110368 A1 * | 5/2010 | Chaum | G02B 27/017 | 351/158 |
| 2010/0328444 A1 * | 12/2010 | Blixt | A61B 3/113 | 348/78 |
| 2011/0013007 A1 * | 1/2011 | Holmberg | A61B 3/113 | 348/78 |
| 2011/0085700 A1 * | 4/2011 | Lee | G06Q 30/02 | 382/103 |
| 2011/0109880 A1 * | 5/2011 | Nummela | A61B 3/113 | 351/210 |
| 2011/0214082 A1 * | 9/2011 | Osterhout | G02B 27/017 | 715/773 |
| 2012/0019662 A1 * | 1/2012 | Maltz | G06F 3/013 | 348/158 |
| 2012/0021806 A1 * | 1/2012 | Maltz | H04W 4/20 | 455/566 |

(56) References Cited

U.S. PATENT DOCUMENTS

2012/0300061 A1* 11/2012 Osman ................ G06F 1/3231
348/135
2013/0083007 A1* 4/2013 Geisner ............... G06T 19/006
345/419
2013/0083173 A1* 4/2013 Geisner ................ G06F 3/013
348/51

FOREIGN PATENT DOCUMENTS

| JP | 2004-113755 | 4/2004 |
|----|-------------|--------|
| JP | 2005-312605 | 11/2005 |
| WO | 2005-046565 | 5/2005 |

* cited by examiner

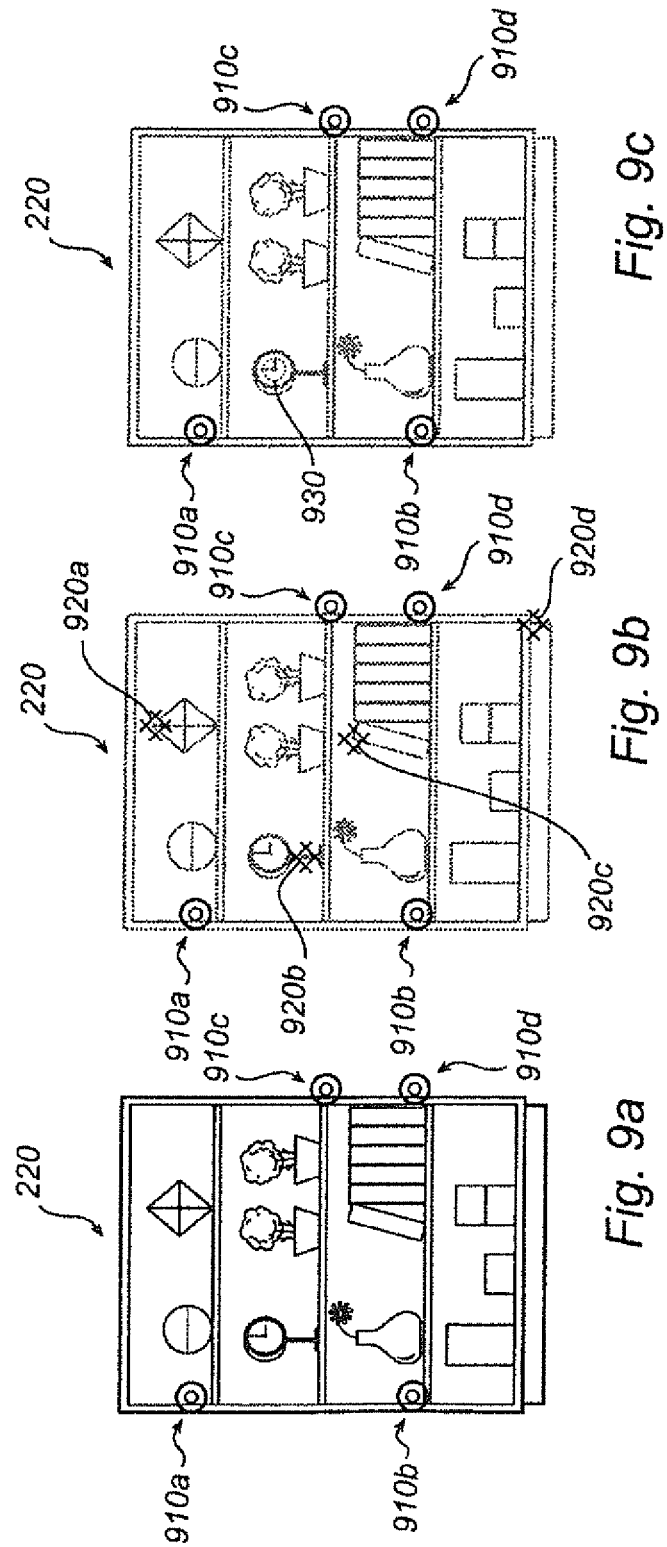

METHOD FOR DISPLAYING GAZE POINT DATA BASED ON AN EYE-TRACKING UNIT

CROSS-REFERENCE TO RELATED APPLICATIONS

This patent application is a continuation of U.S. patent application Ser. No. 13/145,636, filed Jul. 21, 2011, now U.S. Pat. No. 9,495,589, which is a national phase application of PCT Patent Application No. PCT/EP2009/000480, filed Jan. 26, 2009.

FIELD OF THE INVENTION

The invention generally relates to human eye-tracking devices and more particularly relates to a gaze-point detection system which is assisted by reference signals emitted by optical sources provided in the scene under viewing.

BACKGROUND

Monitoring or tracking eye movements and detecting a person's gaze point (as used herein, the point in space at which the person is looking) can be used in many different contexts. Such measurements can be an important information source in analysing the behaviour and consciousness of the person. The information can be used both for evaluating a test scene (as used herein, the visual percept of a region of space in which visible objects or surfaces may be present and inside which a gaze point can be detected) observed by a person, and for evaluating characteristics of the respective person. The diverse uses of gaze point detection include studies on the usability of software and different types of interfaces; evaluation of web pages, advertising and advertisements; provision of means for educating pilots in simulator environments and for training surveillance personnel in security-critical roles; and research in psychology, behavioural sciences and human perception. A field which has attracted an increasing interest in recent years is the evaluation of advertising and other marketing channels. Eye-tracking information may then be gathered from a viewing test person's examination of advertising of a particular merchandise, and the response of the test person is derived. Eye-tracking devices may also be used for collecting information on the response of the viewing person of the placement of a particular article on a shelf of a shop display.

In addition to these applications, there are interactive applications which employ information about the area at which a person is looking in order to respond or react in different ways. For example, the advertising or display of goods in a shop window can undergo a visual change responsive to the detected fact that a person is looking at it. Moreover, a computer system may utilise continuous information on the gaze point of a user to be better capable of displaying the object in which a user is interested and of adapting it intelligently to different behaviours of the user. Thus, an eye-tracker could form part of an interface for human-computer interaction. Since the content of the display is programmed in software, software can also correlate gaze-point information with the semantics of the program.

While eye-tracking-assisted studies of human behaviour up to now have been concerned with a limited number of individuals, many market researchers wish to carry eye-tracking technology over to the statistical, high-volume approach which has historically been very successful in this field. For instance, the cumulated reactions to a particular advertisement campaign of a large number of test subjects may provide an accurate prediction of the efficiency of this campaign during its future, full-scale exposure in society. This emerging use of eye trackers leads to new challenges on the technological level. For instance, available eye trackers are usually complex and fragile devices, and their operation may be demanding—at least to a user having a background in areas such as marketing studies or behavioural sciences rather than a relevant technological field. The applicability of eye-tracking technology to high-volume studies is limited by two facts in particular. Firstly, adapting an eye tracker to a new person may be a time-consuming and technologically demanding exercise, and secondly, many potential test subjects may feel hesitant or reluctant to using such a device if its interface is complicated or physically intrusive.

As seen above, for an equipment to be suitable for gaze-point detection in group studies, it is important that it can switch between the test subjects quickly and conveniently. On a different level, the eye-tracking equipment should also be easily deployable in different environments, and the visual objects to which the test subjects are to be exposed should not be limited to, e.g., computer monitors. Indeed, from the point of view of marketing research, eye-tracking-based studies may be of interest in any environment where consumers receive visual information on which to base their buying decisions, and the range of possible psychological experiments to which eye-tracking technology is applicable seems unlimited.

In conclusion, there appears to be a need for an eye-tracking system which solves at least some of the problems discussed above.

SUMMARY OF THE INVENTION

An object of the present invention is to present gaze-point data of at least one subject detected by an eye-tracking unit.

A method of presenting gaze-point data of at least one subject detected by an eye-tracking unit may comprise presenting a test scene picture acquired by a camera unit, and displaying shapes on the test scene picture. The shapes may represent momentary gaze points of the at least one subject.

The shapes may comprise circles, dots, stars, rectangles and/or crosses. A size of each shape may vary to indicate accuracy of the gaze-point data.

The momentary gaze points may be acquired by the eye-tracking unit over a time interval of non-zero length. The method may further comprise displaying textual annotations specifying a respective time of viewing of the momentary gaze points. The method may further comprise displaying lines or arrows connecting the shapes to specify an order of the momentary gaze points.

A color of the shapes may indicate a dwell time of the at least one subject's gaze. The shapes may represent a sum of dwell times of a plurality of subjects.

The method may further comprise predefining a plurality of areas of interest in the test scene picture. The dwell time of one or more subjects in each area of interest may be accumulated.

The method may further comprise superimposing shaded areas of interest in accordance with statistical measures of the dwell times of the one or more subjects. The statistical measures may comprise a mean total dwell time per test subject, a mean duration of each fixation, percentiles of the total dwell time and/or percentiles of a test population having visited each area of interest.

A video sequence may be constructed based on the test scene picture in combination with an IR signal source tracking data provided by the eye tracking unit by applying perspective transformations.

A plurality of test scene pictures acquired at regular intervals forming a video sequence may be presented. Shapes on respective frames of the video sequence may also be displayed.

Another aspect of the present invention is to provide a device for detecting gaze point in a test scene. Such a system may comprise at least four functionally separate parts:

one or more infrared (IR) signal sources to be placed in a region of space (test scene) currently studied for use as spatial reference points;

at least one pair of eye glasses to be worn by a person (test subject) and having the double capability of detecting the IR signals and tracking eye movements of the person;

a data processing and storage unit for calculating a gaze point of the person; and a scene camera for acquiring a picture of the test scene.

The scene camera may be an external device or may be integrated in the eye glasses as a camera unit. Although the inventors consider these two embodiments equally useful, the present disclosure will focus on the case where the scene camera is integrated in the eye glasses. This is not intended to limit the scope of the invention, nor to indicate a preference towards embodiments having this characteristic. In fact, most references to 'camera unit' may quite simply be replaced by 'scene camera' where appropriate.

Output of a system according to the invention includes a signal indicative of a gaze point of the test subject. The gaze point is presented relative to a picture of the test scene, in which one or more IR signal sources have been positioned and are operable to emit IR light. Each of the one or more pairs of eye glasses has an image sensor adapted to receive the IR signals from the at least one IR signal source and to generate an IR signal source tracking signal corresponding to the detected IR signals. Each pair of eye glasses secondly includes an eye-tracking unit adapted to determine the gaze direction of an eye of said person and to generate an eye-tracking signal corresponding to the detected gaze direction. Thirdly, each pair of eye glasses comprises a camera unit (unless this is embodied as an external scene camera) adapted to acquire at least one picture of the region of space, relative to which the gaze point is determined. The data processing and storage unit is adapted to communicate with a pair of eye glasses according to the invention, so as to obtain the at least one IR signal source tracking signal (from the image sensor), the eye-tracking signal (from the eye-tracking unit) and the at least one picture (from the camera unit). The data processing and storage unit is further adapted to calculate a gaze point of the person with respect to one of said at least one acquired picture as a function of the at least one IR signal source tracking signal, the eye-tracking signal and the at least one picture. The gaze point may then be indicated directly in the picture of the test scene, which is an intuitive and ready-to-use presentation format.

A system according to the invention is easy to set up, is failsafe and provides accurate gaze-point data. Part of the robustness of the measurements is owed to the eye glasses' capability of jointly determining the locations of the IR signal sources and the gaze direction of a person wearing the glasses. The camera unit of the eye glasses (or, respectively, the external scene camera) is adapted to provide a picture of the test scene, relative to which a gaze point can be calculated. Preferably, the eye-tracking unit and the image sensor are rigidly connected to the eye glasses or to one another. This is because their measurements are performed in separate reference frames, which would lack a stable interrelation if their relative orientations and positions were allowed to change between or during measurements. In alternative embodiments, wherein the eye-tracking unit and the image sensor are mobile with respect to one another, there are provided position and orientation indicators or functionally equivalent devices to furnish the information needed for interrelating the reference frames.

The IR signal sources, at least when arranged in a protective housing and provided with suitable fastening means, can be deployed in a very wide range of imaginable test scenes, which provides a high degree of versatility. Moreover, most test subject are accustomed to sun glasses or other spectacles and therefore feel comfortable when wearing the eye glasses of the inventive system. The latter do contain sophisticated technological devices, but have the familiar appearance of a regular pair of eye glasses, allowing a test subject to relax and behave naturally during measurements.

The system is scalable by virtue of the possibility of providing multiple pairs of eye glasses, for a limited number of available sets of individual equipment may be a bottleneck in studies comprising a large number of test subjects. It is expedient in such studies to provide wireless communication links between eye glasses and the rest of the system. The system also has a favourable scalability on the data processing level, for the data processing and storage unit can easily be adapted to calculate the gaze points of all test subjects relative to one picture of the test scene. This is an intuitive and immediate presentation format and also avoids the tedious task of manually comparing different view of the test scenes in order to summarise gaze point information for different test subjects. In this connection, it should be emphasised that the three functional parts of the system are not necessarily physically separate. Following the general tendency towards miniaturisation and weight reduction, the data processing and storage unit may be physically embodied in an IR signal source, in a pair of eye glasses or in some other component of the system. It is also possible to combine the image sensor with a camera unit or external scene camera that is sensitive for IR radiation; most silicon-based digital cameras have good responsivity in the near IR spectrum. In embodiments adapted for use in studies comprising a large number of test subjects, however, the data processing and storage unit is preferably centralised for the sake of scalability. This way, although the data have been gathered in a distributed fashion (possibly using several pairs of eye glasses), the data are ultimately accumulated in one location for further processing. In particular, although the camera unit(s) are capable of acquiring a unique picture of the test scene for each test subject, the calculated gaze points of different test subjects are most useful when presented relative to one picture of the test scene. In embodiments where the data processing and storage units consists of physically distributed sub-units, these latter make a collective decision on which picture to use.

There are further provided, in accordance with a second and third aspect of the invention, a method for detecting a gaze point of a person relative to a picture of a region of space and a computer program product.

In one embodiment, the data processing and storage unit is adapted to produce a combined picture of the test scene and the positions of the IR signal source(s). The positions of the IR signal sources are useful as precise reference points in the coordinate system of the picture, so that the detected gaze point(s) can be represented with high accuracy.

The system may be adapted to utilise other reference points in addition to the IR signal sources in determining the position of the eye glasses relative to the test scene. In particular, tracking of image features, such as edges, corners and ridges, may meritoriously complement tracking of the IR signal sources. This is especially useful after the initial detection of the positions of the IR signal sources, so that the positions of such image features can be determined relative to the IR signal sources.

The IR signal sources may emit modulated IR light for thereby being distinguishable from one another. In other words, the IR signal sources transmit multiplexed signals over the IR spectrum. This facilitates processing of the IR signal source tracking signals generated by the image sensor. Suitable modulation schemes include modulation with respect to time, such as frequency modulation, pulse-width modulation and modulation by orthogonal codes. Alternatively, the IR signal sources are synchronised and adapted to emit signals in separate time slots of a repetitive time frame. As another alternative, optical modulation can be used, wherein the IR signal sources emit at different wavelengths, such as 750 nm, 850 nm and 950 nm, and absorption filters or dielectric filters are provided at the IR sensors to separate the sources. As yet another alternative, IR signal sources can be made distinguishable by having different polarisation characteristics.

The IR image sensor of the eye glasses may comprise a sensor surface, which is preferably plane, and which is arranged at some known distance from an optical aperture, such as a fixed or variable diaphragm, of the image sensor. This way, all light rays incident on the sensor surface will pass essentially through a common point, namely the centre of the optical aperture in the case of a pinhole camera model. In Gaussian optics, nodal points define the incident angles of the IR beams. It is further possible to detect a position of the signal on the sensor surface. The position of the signal may be a peak-intensity point, in which the maximal intensity is received or the centroid for sub-pixel resolution. Alternatively, if the sensor surface makes detections in a binary fashion with respect to some intensity threshold or if the pixels tend to become saturated frequently, the geometrical centre of the illuminated spot can be used as a signal position. On the basis of the centre of the optical aperture, the signal position and the separation between the optical aperture and the sensor surface, the angle of incidence of the light ray can be calculated. Preferably, this signal is incorporated in the IR signal source tracking signal generated by the image sensor.

The eye-tracking unit of the eye glasses may comprise the following sections: one or more devices adapted to emit IR or near-IR light, preferably arranged on a sidepiece of the eye glasses and directed towards an eye of the person wearing the glasses; a detector for acquiring an image of the eye, the detector preferably being arranged on a sidepiece of the eye glasses; and an evaluation unit for processing the acquired image of the eye and thereby determining a gaze direction of the eye. Preferably, the device for emitting IR or near-IR light to illuminate an eye of the person is directed towards the eye via reflection on one of the transparent plates of the eye glasses, which then acts as a partial IR mirror or may have an IR-reflective coating. The detector is adapted to receive only light at the wavelength of the IR-light-emitting device, so that the eye is imaged using only active illumination. To achieve such wavelength discrimination, a filter for removing light in the visible spectrum, such as a (low-pass) absorption filter, may be provided in front of the detector. Since the described eye-tracking unit is located closely to the eye, it would be delicate to arrange illumination and detection means coaxially, for thereby enabling eye tracking in the bright-pupil state (the familiar 'red-eye effect') caused by retinal reflection. Therefore, preferably, the IR-light-emitting device and the detector are arranged on separate optical axes, so that the eye is imaged in its dark-pupil condition.

According to an embodiment of the present invention, the eye glasses are provided with a first polarisation filter before at least one eye of the test subject. This may be advantageous in cases where the gaze detection system is used outdoors. Suitably, the polarisation filter is provided as a layer on the plates (lenses) of the eye glasses. Optionally, a second polarisation filter, the transmissive direction of which is perpendicular to that of the first polarisation filter, is arranged in front of the detector of the eye-tracking unit. This way, the detector is blocked from any light which has been polarised by the filter on the plates, thus amplifying the relative intensity of light from the IR-light-emitting device; external light could otherwise cause excitation of the detector and disturb the measurements. As an additional advantage, the first polarisation filter may attenuate uncomfortable sunlight reflexes on horizontal surfaces from reaching the test subject's eyes. The first filter will be particularly efficient in this respect if its transmissive direction is essentially vertical during wear, as the vertically polarised component of such reflected sunlight is usually faint.

To save weight and volume, certain components needed for the operation of the eye glasses can be located in a physically separate support unit, which can be hung from a belt worn by the test subject or placed in a pocket. Such support unit, which is communicatively coupled to a pair of eye glasses, may contain a voltage source (such as a solar cell or battery), a data buffer for storing information collected during measurements, a processing means for performing pre-processing of data (such as data compression or conversion to a suitable format), a wireless transmitter/receiver adapted to communicate with the associated pair of eye glasses and/or with the data processing and storage unit.

The image sensor of the eye glasses may consist of two orthogonal line sensors, the scanning directions of which are preferably arranged parallel with the frontal plane of the test subject during wear of the eye glasses. The scanning direction of one of the line sensors may be vertical, but is preferably rotated by an angle of 3-30 degrees. In practical situations, it is often convenient—and sometimes necessary—to arrange IR sources aligned along a vertical or horizontal line; see, e.g., FIG. 2, wherein IR signal sources 800c and 800d are located approximately on equal height. Two sources may then give rise to a degenerated signal if the scanning direction of the line sensor is perpendicular to such line. The disclosed arrangement of the line sensor scanning directions makes this event less probable.

According to an embodiment of the present invention, at least one IR signal source of the system is operable in an energy-saving mode or standby mode. Since it is important that the IR signal sources are flexible and easy to deploy in various test environments, they are preferably battery-powered. To increase time between battery chargings or replacements, an IR signal source may be adapted to enter the energy-saving mode after the typical duration of a test session. The IR signal source can be reactivated by receiving, suitably via a wireless communication means, a predefined signal from a pair of eye glasses or from the data processing and storage unit. To further reduce energy consumption, the IR signal source preferably comprises a passive receiving means adapted to convert incident electromagnetic radiation into an amount of electric energy sufficient to actuate the IR signal source into its operation mode. The eye glasses may then comprise means for emitting such electromagnetic radiation.

In situations where a large number of test subjects participate in an eye-tracking-assisted study, efficient collection and presentation of the data are essential. Hence, a system according to the invention—and adapted with special regard to such studies—may comprise a plurality of individual user equipments (several pairs of eye glasses), so that more than one user at a time can look at the test scene while being monitored with respect to gaze point. Most expediently, however, such a multi-subject system comprises one single data processing and storage unit, so that gaze-point information for all users is gathered in one location. This facilitates statistical analysis of the entire amount of gaze-point information. Additionally, gaze-point data for all test subjects can be conveniently presented with respect to a single picture of the test scene, the picture being acquired by any one of the eye glasses of the system or by an external imaging device, as appropriate.

These and other aspects of the invention will be apparent from and elucidated with reference to the embodiments described hereinafter. All terms used herein are to be interpreted according to their ordinary meaning in the technical field, unless explicitly defined otherwise herein.

BRIEF DESCRIPTION OF THE DRAWINGS

Embodiments of the present invention will be described with reference to the accompanying drawings, on which:

FIG. 9a is a combined picture of a region of space (test scene) which includes the positions of the IR signal sources;

FIG. 9b is the combined picture of FIG. 9a, further including indications of image features suitable for being tracked;

FIG. 9c is the combined picture of FIG. 9a, further including indications of gaze points of a test subject, as measured by a system according to the present invention;

DETAILED DESCRIPTION OF EMBODIMENTS OF THE INVENTION

Figure 1:
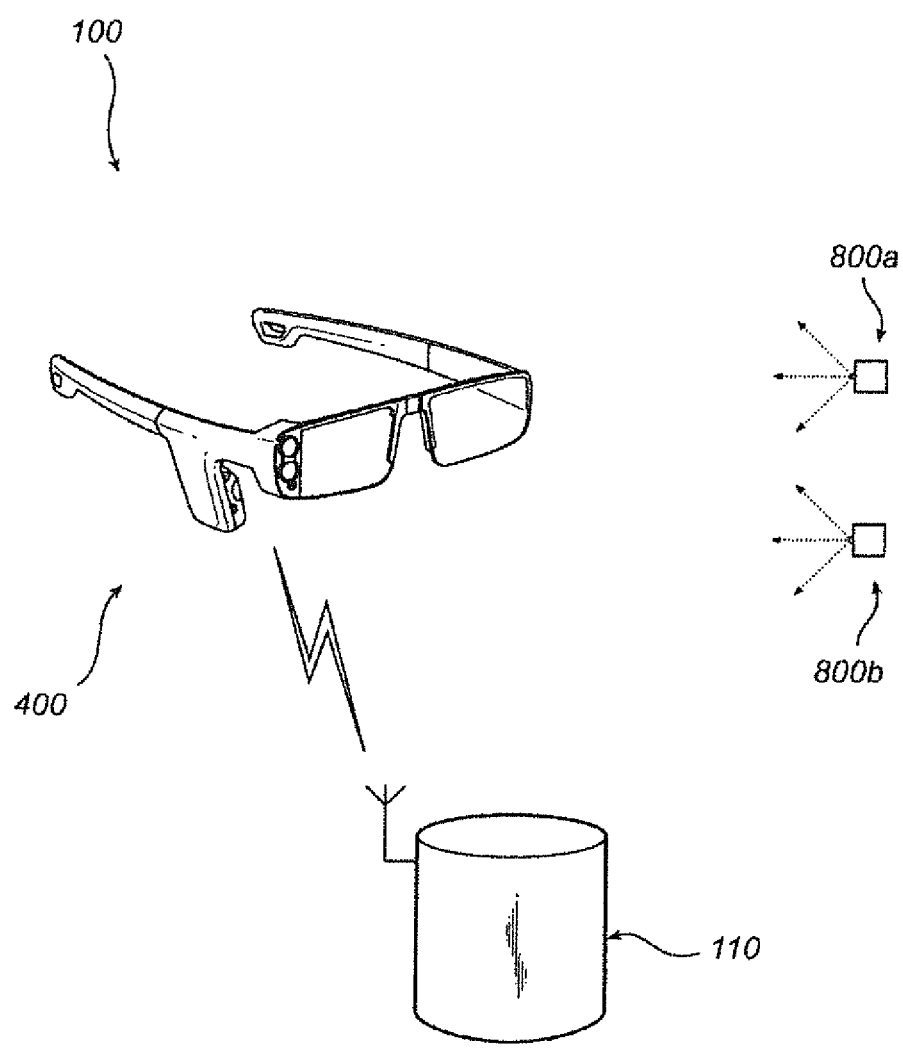
FIG. 1 is a schematic drawing of a system for detection of a gaze point of at least one person, according to an embodiment of the invention.

With reference generally to FIGS. 1-8, the constituent parts of a gaze-point detection system 100 according to the invention will now be described. As shown in FIG. 1, the system 100 includes a pair of eye glasses 400, two IR signal sources 800 (although the system could have included any number of IR signal sources) and a data processing and storage unit 110. The IR signal sources 800 are adapted to emit IR light which can be received by the eye glasses 400. The eye glasses 400 on their part are operable to communicate (uni- or bidirectionally) with the data processing and storage unit 110.

Figure 2:
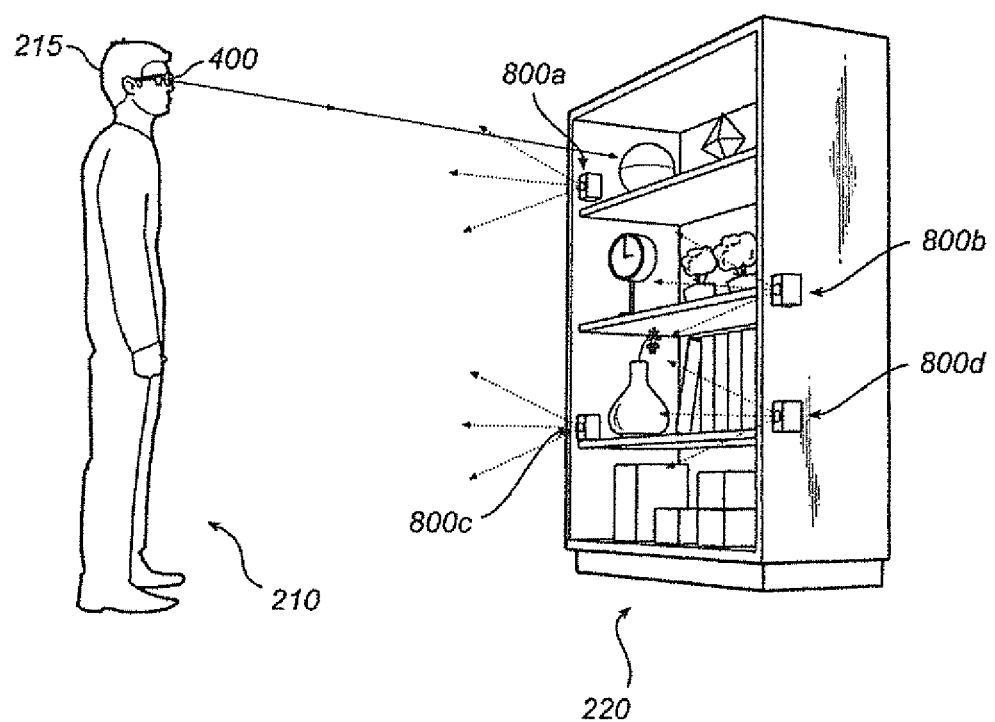
FIG. 2 shows the system of FIG. 1 applied to an exemplary measurement situation.

FIG. 2 shows the same system 100 applied to an exemplary measurement situation. The eye glasses 400 of FIG. 1 are worn by a person (test subject) 210. The eye glasses 400 are adapted to fit snugly onto the person's 210 head 215, so that little relative movement is possible. If the eye glasses 400 are overly mobile with respect to the head 215 of the person 210, then the accuracy of the gaze-point measurements can be threatened, especially in case of sudden head movements or vibrations. Slow movements, however, usually do not cause any problems, since the eye-tracking unit repeatedly measures the position of the eye along with the gaze direction. As indicated in FIG. 2, the IR light generated by each of IR signal sources 800 is not concentrated in a narrow ray but is emitted over a wide solid angle, such as a half-sphere. This allows the test subject 210 to be positioned in a variety of points on the ground, and also avoid the need for readjustment of the IR signal sources 800 if, for instance, a tall test subject follows a short one, or if some test subjects prefer to watch the test scene from a sitting position while others rather stand. The data processing and storage unit 110 can be embodied as a general-purpose computer with computing and storage capabilities as well as communication means adapted to connect to other constituent parts of the system, particularly eye glasses, in order to receive and/or transmit data.

In the exemplary situation shown in FIG. 2, four IR signal sources 800 are arranged in a bookcase 220 containing visible objects: a sphere, an octahedron, a clock, plants, a vase, various books and rectangular boxes. The bookcase with its objects is the test scene of this exemplary situation. The system's 100 presentation of the gaze point of the person 210 is related to the plane in which the IR signal sources 800 are located, which approximately corresponds to the front plane of the bookcase 220.

Figure 3:
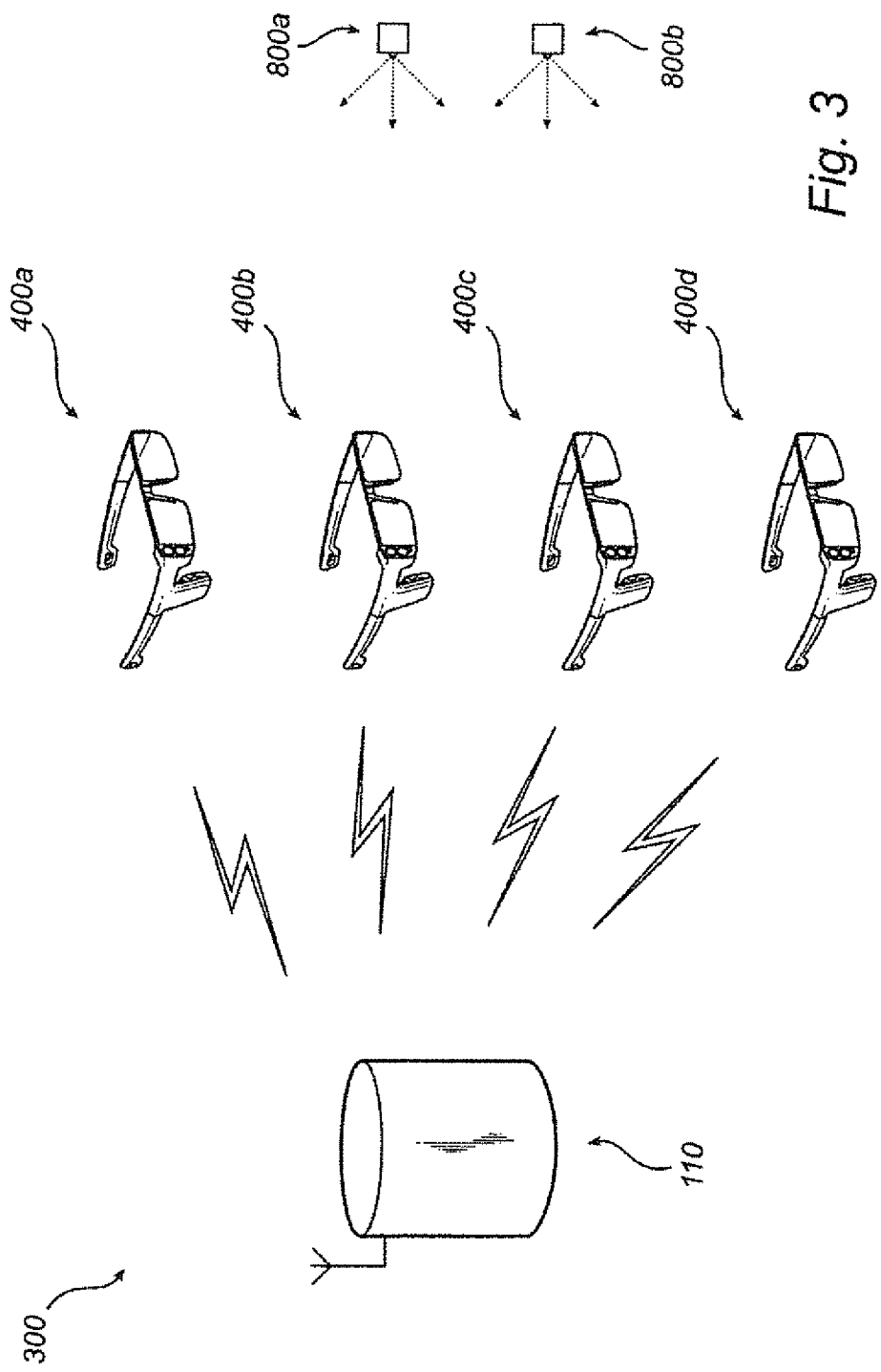
FIG. 3 is a schematic drawing of a system according to the invention and adapted to detect gaze points of a plurality of test subjects.

FIG. 3 shows a gaze-point detection system 300 adapted to be used by a large number of test subjects. Like the system 100 of FIG. 1, it includes a data processing and storage unit 110 and a plurality of IR signal sources 800. To expedite the data collection by allowing several test subjects to be measured at one time, the system 300 comprises several pairs of eye glasses 400, which are functionally equivalent but may differ as regards size, colour etc. As already noted, the IR signal sources 800 emit IR light in a multidirectional fashion, so that the test subjects on which measurements are currently being performed are free to choose their viewing positions within a reasonably large area facing the test scene.

Figure 4:
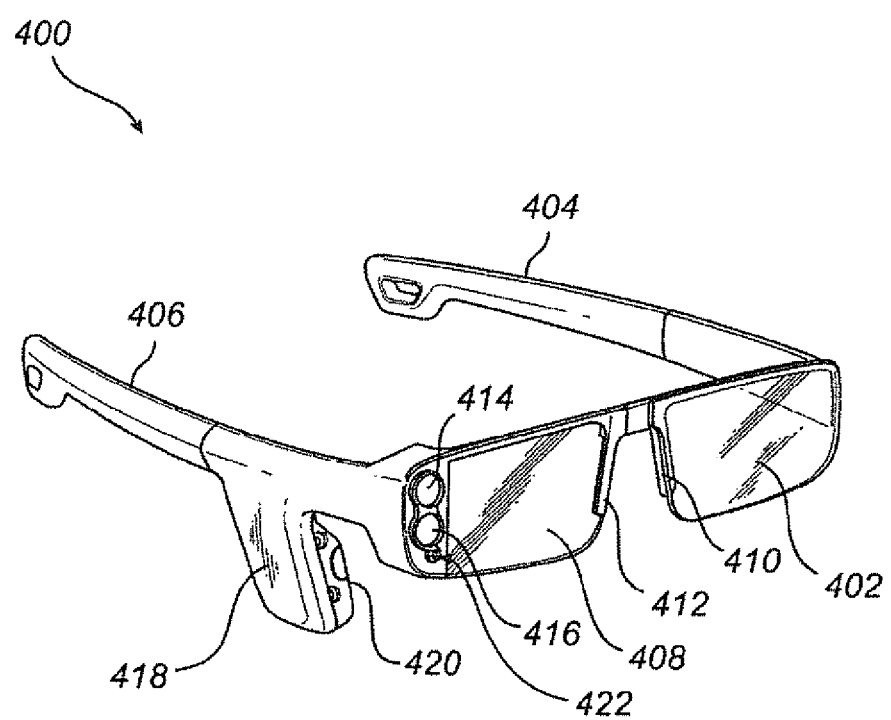
FIG. 4 is a perspective view of a pair of eye glasses for use in a detection system according to the invention.

FIG. 4 depicts details of the eye glasses 400, the main tasks of which are to sense the gaze direction of a person wearing them, to receive IR reference signals from the direction of the test scene and to acquire a picture of the test scene. In order to enhance data quality, it is important that the eye glasses 400 are not too mobile with respect to the head of the person during a measurement session. When the eye glasses 400 are worn, sidepieces 404, 406 of the eye glasses 400 rest on the ears of the person, and nose plates 410, 412 rest on an upper portion of the person's nose. Preferably, the sidepieces 404, 406 are somewhat elastic and exert a small inward force, thereby keeping the eye glasses 400 in place during movements of the person's head. The design of the sidepieces 404, 406 is of little consequence to the operations associated with the gaze-point detection, the one shown in FIG. 4 being intended as an example. Preferably, the nose plates 410, 412 are of such shape and material that the lateral mobility is limited and annoying slipping of the eye glasses 400 down the nose is prevented. The eye glasses 400 also comprise visually transparent plates 402, 408. One acts as a mirror for an IR detector (not shown) adapted to image an eye of the person, whereas the other could in principle be omitted, for unless the intended wearer of the eye glasses 400 suffers from some defect of vision, the visually transparent plates 402, 408 have zero refractive power. An IR mirror is deposited on at least one of the visually transparent plates 402, 408 using a stack of thin film coatings having negligible interference in the visible spectrum. The mirror is deposited on the side facing the eye during wear. The plates 402, 408 add some weight to the eye glasses 400, increasing their mechanical stability. They may also serve a pedagogical purpose in so far as the wearer instinctively positions the eye glasses 400 according to his or her habit of wearing other eye glasses. Particularly, a correct position of the eye glasses 400 implies that the eye-to-plate distance is not uncomfortably small and that the plates 402, 408 are orthogonal to a relaxed gaze direction of the person, thus essentially parallel to the frontal plane FP (cf. FIG. 6) of the wearer. A projection 418 on the right side piece 406 may contain equipment (not shown) associated with the data gathering, such as an evaluation unit, pre-processing means, a voltage source and means for communicating with other components of the system 100.

The eye glasses 400 comprise several measuring devices. Firstly, an eye-tracking unit (not shown) is provided. As a part of the eye-tracking unit (not shown), an IR light source 420 for illuminating the right eye by invisible IR light is provided on the projection 418. The eye glasses 400 shown in FIG. 4 are adapted to track the gaze direction of the right eye, but a variant for tracking the left eye, or both, would be equally useful. A detector (not shown), which is too provided on the projection 418, is adapted to repeatedly acquire (via reflection off the right plate 408) an image of the right eye illuminated by the light source 420. From each image, information can be extracted for determining the gaze direction. This information may be location of the light-source reflection (glint) on the cornea and the position of the pupil or, after processing, the location of the cornea and the orientation of the visual axis of the eye. Extraction of the gaze point direction, which may be performed by an evaluation unit (not shown) if such is provided, may be effectuated according to any of the algorithms known in the art. The gaze direction can be expressed in terms of linear coordinates in a two-dimensional image plane which moves with the eye glasses; then, more precisely, the gaze direction is the point at which the visual axis of the eye intersects this image plane. To facilitate subsequent data processing, the locations of the IR signal sources are suitably expressed in the coordinate system of the same image plane. Alternatively, the detector (not shown) could have been arranged on the projection 418 or on a portion of the sidepiece 406, from which the eye is visible. Care should be taken, especially if the detector (not shown) is arranged on the projection 418, that the detector is not coaxial or nearly coaxial with the light source 420. This could otherwise cause a retinal reflection, leading to an undesired bright-pupil effect in some gaze directions. The measurement data from the eye-tracking unit (not shown) are output as an eye-tracking signal.

Secondly, an image sensor 416 is provided on a frontal side of the eye glasses 400, suitably under a protective transparent plate. The transparent plate may be adapted to block shorter wavelengths, and may be a low-pass filter, alternatively a band-pass filter centred around the IR signal centre wavelength. The image sensor 416 is adapted to receive at least one IR signal for use as a reference in determining the location of the test scene relative to the eye glasses 400. The image sensor 416 is preferably adapted to ignore other IR signals than those emitted by the IR signal sources 800 of the system 100 for gaze-point detection; signals proper to the system can be distinguished from other IR radiation by being modulated with respect to time, frequency or polarisation. The image sensor 416 may not only detect the presence of a given IR signal, but can also measure its angle of incidence on the image sensor 416, so that the line of sight to the signal source can be derived. Moreover, modulation of the received IR light can be encoded, so that identities of IR signal sources can be determined on a later processing stage, such as in the data processing and storage unit. The measurement data from the image sensor 416 is output as an IR signal source tracking signal. Particulars of the image sensor 416, and suitable variants of it, will be described below with reference to FIGS. 6 and 7.

Thirdly and finally, a camera unit 414 is provided on a frontal side of the eye glasses, preferably under a protective transparent plate. Both the image sensor 416 and the camera unit 414, which are immobile with respect to the eye glasses 400, are situated closely to the (visual axis of the) eye of which the gaze direction is detected, so as to minimise parallax errors. It is noted that the positions of the image sensor 416 and the camera unit 414 may be reversed without any functional inconvenience. The camera unit 414 is adapted to acquire at least one picture of the test scene in the visible spectrum, which does not include IR radiation. Because the separation of the eye and the camera unit 414 is small, any picture of the test scene acquired by the camera unit 414 corresponds approximately to the visual perception of the person wearing the eye glasses 400 at that point in time, at least if the person is not diverting his or her gaze from the relaxed direction.

Figure 14:
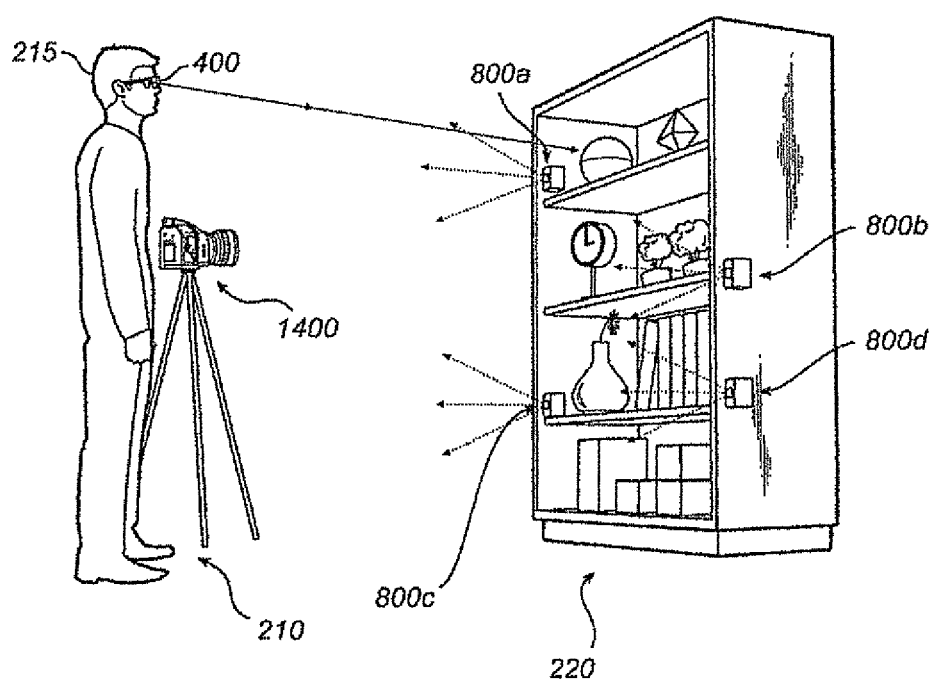
FIG. 14 shows a variant of the system of FIG. 1, wherein an external scene camera is used for taking the test scene picture, when applied to an exemplary measurement situation.

FIG. 14 shows an alternative embodiment of the system, wherein the eye glasses do not comprise an active camera unit. The picture (snapshot) of the test scene is instead acquired by an external scene camera 1400. In a picture thus acquired, the locations of the IR signal sources are entered by a user before the final data processing step. Alternatively, the scene camera 1400 is adapted to receive both visible light and IR light, yielding a combined image, in which both the visual percept of the scene and the locations of the IR signal sources can be seen.

The data collected by the eye-tracking unit (not shown), the image sensor 416 and the camera unit 414—namely, the eye-tracking signal, the IR signal source tracking signal and the at least one picture may be stored in the eye-glasses temporarily, or may be transmitted over a wired or wireless communication link to the data processing and storage unit 110 of the system 100. The measurement data are generally time-stamped, so as to facilitate further processing and presentation. The time stamps may be generated on the basis of local clocks provided in data-generating parts of the system 100. The local clocks may be synchronised with respect to a master clock (which may be a designated local clock) by transmitting a synchronisation signal over the communication links already present in the system 100.

In a particular embodiment, the frontal side of the eye glasses 400 is provided with an activation signal transmitter 422, which is operable to transmit a wireless activation signal—e.g., IR, optical, acoustic and even radio-frequency—towards an expected location of an IR signal source. It is advantageous to use a directive activation signal such as an optical signal, which makes it possible to activate the IR signal sources in one test scene separately from those of other test scenes even if these are arranged in spatial proximity of each other. Indeed, if this IR signal source is in a standby mode which can be interrupted by such activation signal (this is detailed below with reference to FIG. 8), then the IR signal source goes back to its operational mode, which includes emitting an IR signal that can be used as a reference signal.

Figure 5:
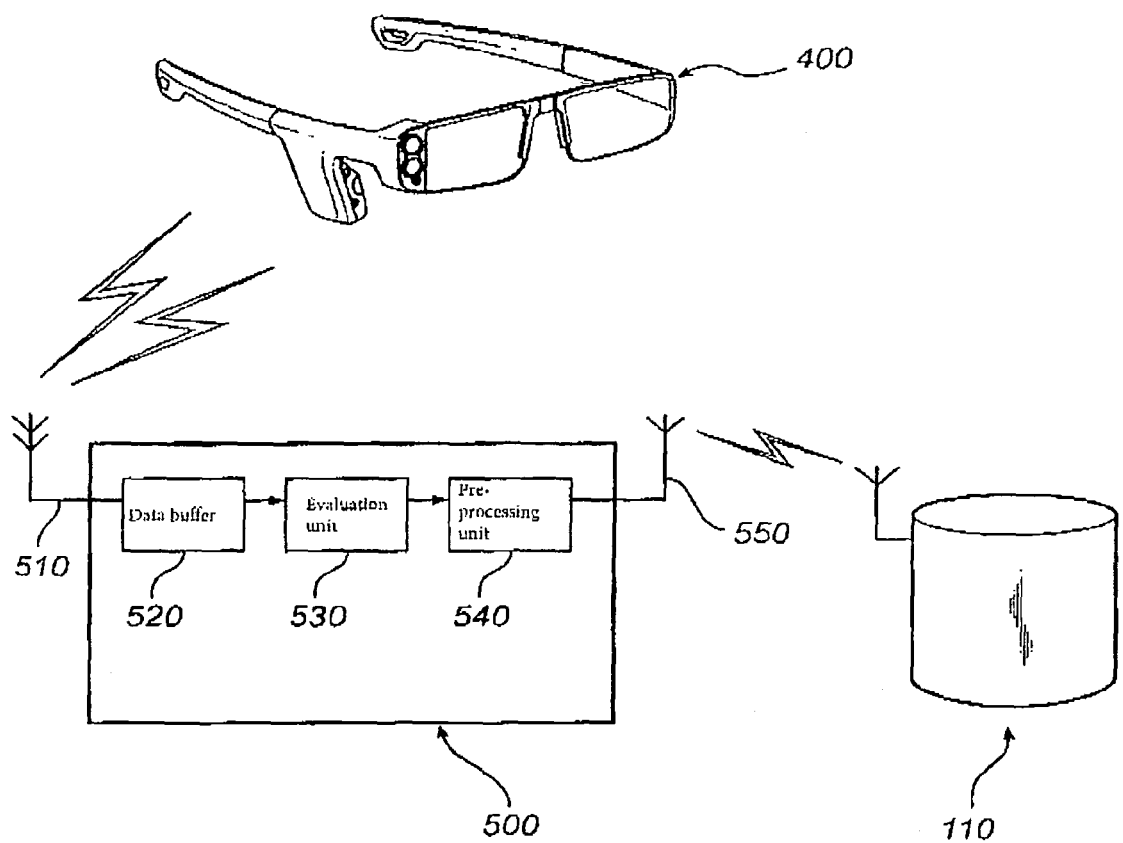
FIG. 5 is a schematic drawing of a pair of eye glasses with an associated support unit, according to an embodiment of the invention.

FIG. 5 shows an alternative embodiment of the eye glasses 400, wherein the eye glasses 400 are adapted to communicate with a support unit 500, in which pre-processing and (partial) evaluation of measurement data are performed. In this embodiment, the communication is wireless and takes place by means of a transceiver 510 at the support unit 500 and another transceiver (not shown) at the eye glasses 400, which is preferably arranged in the projection 418. Alternatively, a wired connection is provided between the eye glasses 400 and the support unit 500. The eye glasses 400 generally have the same measuring means as in FIG. 4, notably IR light source 420, detector (not shown), image sensor 416 and camera unit 414. However, some components have been located to the support unit 500 in order to extend battery time and enhance comfort of the wearer. Relocating the heavier components away from the eye glasses particularly reduces the risk of a laterally skew mass distribution that would otherwise call for counterbalancing which could make the eye glasses 400 bulky and heavy. The support unit 500 may be hung from a belt worn by the wearer of the eye glasses 400. In this embodiment, the support unit 500 comprises a data buffer 520, an evaluation unit 530 for extracting gaze-direction information from the eye-tracking signal, and a pre-processing means 540 for converting the data to a format suitable for being transmitted to the data processing and storage unit 110. The support unit 500 further comprises a rechargeable battery (not shown), a main power switch (not shown), an actuator (not shown) for the activation signal transmitter 422 of the eye glasses 400, and a transceiver 550 for communicating with the data processing and storage unit 110. Since the distances from the support unit 500 to the eye glasses 400 may differ considerably from the distance to the data processing and storage unit 110, the two communication links may use different technologies, such as Bluetooth® technology for the shorter-range communication link and wireless local area network (WLAN) technology for the longer-range communication link. Alternative embodiments of the support unit 500 may comprise a local storage unit, such as a memory card, for buffering data; then, particularly if the data is ultimately transmitted to the data processing and storage unit 110 in a wired fashion, the transceiver 550 may not be necessary.

Figure 6:
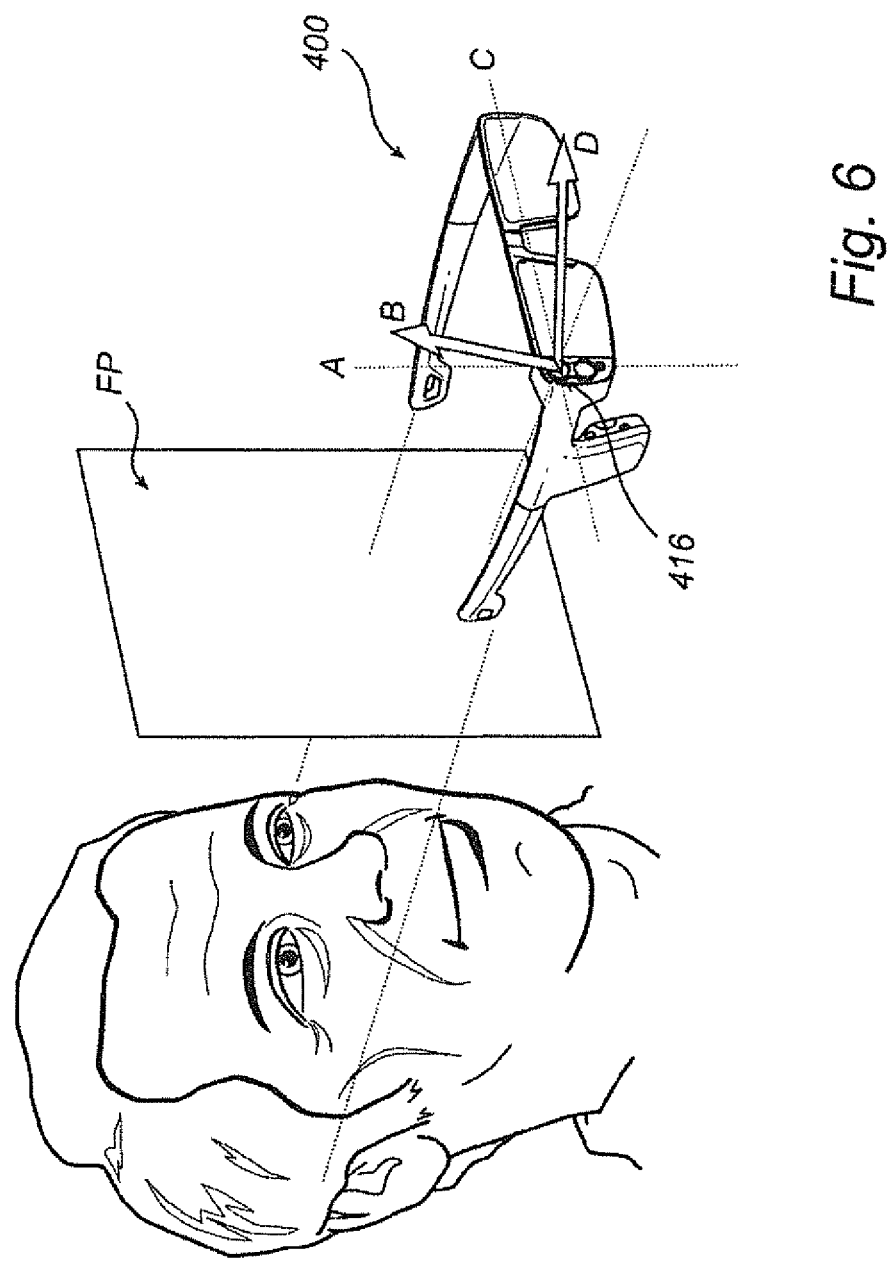
FIG. 6 is a detail view of the eye glasses of FIG. 4, wherein the directions of the scanning directions of the line sensors are indicated.

A more detailed description of a currently preferred embodiment of the IR image sensor 416 of the eye glasses 400 will now be given. The image sensor 416 is composed of two orthogonal line sensors, from the output signals of which the reception direction (expressible as two angles, because the apparent position of an IR signal source has two degrees of freedom) and identity of an IR signal can be determined. The reception direction can be expressed as two angles, because the apparent position (the projection onto the plane of the test scene) of an IR signal source has two degrees of freedom. As used herein, a line sensor is a directional light sensor, which outputs a received signal as a function of a coordinate measured along a scanning direction of the sensor. Thus, contributions from any two light sources located at the same coordinate—that is, on a line perpendicular to the scanning direction will be summed by the line sensor. On the basis of signals from two line sensors that are orthogonal (or at least have distinct scanning directions), the two angles (or, equivalently, image plane coordinates) characteristic of the reception direction can be determined. In this embodiment, the line sensors are positioned so that their respective scanning directions are orthogonal and are parallel with the frontal plane FP of the person wearing the eye glasses 400, as shown in FIG. 6. As an inventive feature, the scanning directions of the line sensors do not exactly coincide with the vertical A and horizontal C directions. Instead, for reasons outlined in previous sections of the present disclosure, it has been found preferable to arrange the line sensors in a slightly rotated fashion, so that each of the scanning directions B, D differs by an angle of 3-30 degrees from the vertical A and horizontal C directions.

Figure 7:
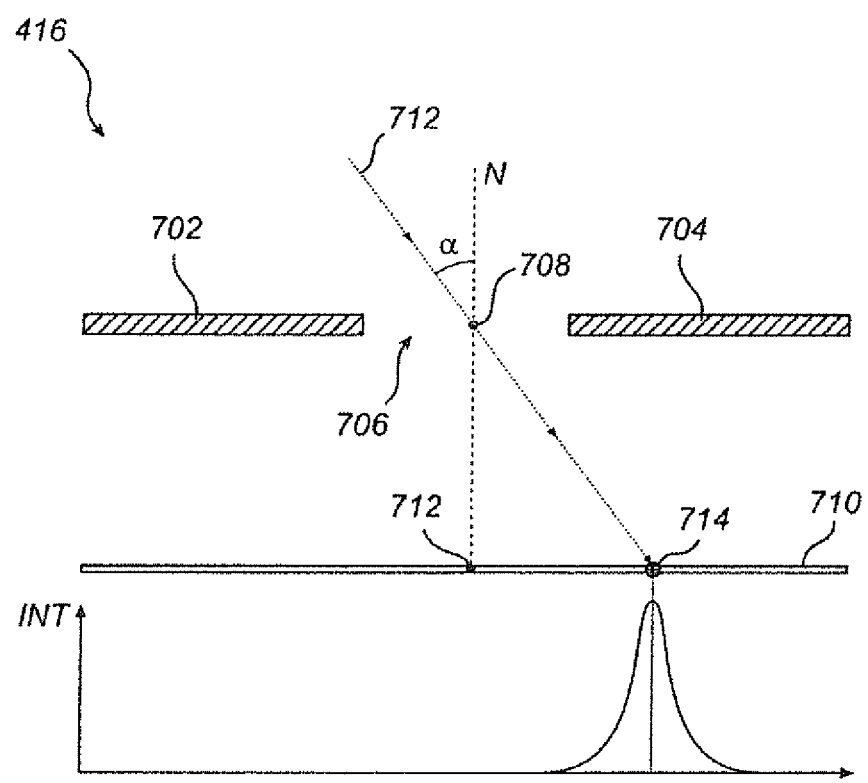
FIG. 7 is a cross-sectional view, in the plane of an incident light ray, of an angle-discriminating image sensor according to the invention.

FIG. 7 is a cross-sectional view of the image sensor 416 as seen in the plane of an incident IR light ray 712 and a normal axis N of an IR-light sensitive surface 710 of the line sensor. The scanning direction of the line sensor extends in the left-right direction of the drawing, implying that the sensor sums contributions from sources situated on any line orthogonal to the plane of the drawing. Portions 702, 704 of a diaphragm define an optical aperture 706 into the image sensor 416. In the figure, the normal axis N of the surface 710 has been drawn through a centre 708 of the optical aperture 706. For simplicity of the drawing, the sensor 416 is represented according to a pinhole camera model, which means in particular that the nodal points and the centre 708 of the aperture 706 coincide. More elaborate models having separate nodal points can be conceived and implemented as a simple variation of the disclosed embodiment. The line sensor outputs a received intensity INT for each coordinate of the sensor surface 710, as indicated by the curve drawn underneath. It is clear from the curve that the received intensity is maximal at a peak-intensity point 714. The distance between the optical aperture 706 and the light-sensitive surface 710 is known a priori. By determining also the distance from the peak-intensity point 714 to the projection 708 of the centre 708 onto the light-sensitive surface 710, the system can obtain the angle α of incidence of the incident light ray 712. For sub-pixel resolution centroid calculation can be used to determine 714. As explained in connection with FIG. 6, a second line sensor, orthogonal (within approximation) to the first line sensor 710, can be similarly provided around the same optical aperture centre 708 to provide a second angle of incidence, thus completely characterising the direction of incidence of the ray 712. As is known to those skilled in the art, the direction of incidence (a pair of angles) is equivalent to a pair of coordinates in an image plane of the two sensors.

As noted in earlier sections, the peak-intensity point is but one way to define the position of the signal on the sensor surface 710. It is also possible, and perhaps more suitable if two or more pixels share the maximal intensity, to retrieve the geometric centre of the illuminated spot. The centre may be computed as a centroid weighted by the local intensity value at each pixel in the illuminated spot. The centroid position is given by the following formula:

$$x_{centroid} = \frac{\sum_i x_i \times INT_i}{\sum_i INT_i},$$

where $x_i$ is the coordinate and $INT_i$ is the intensity reading of the $i^{th}$ pixel. Furthermore, if the point-spread function of the sensor is known, the received signal pattern may be de-convolved with respect to this function in order to retrieve the pre-image of the sensor. To enhance accuracy, the darkness current of the sensor, as determined in a calibration step, may be subtracted prior to other signal processing.

Figure 8:
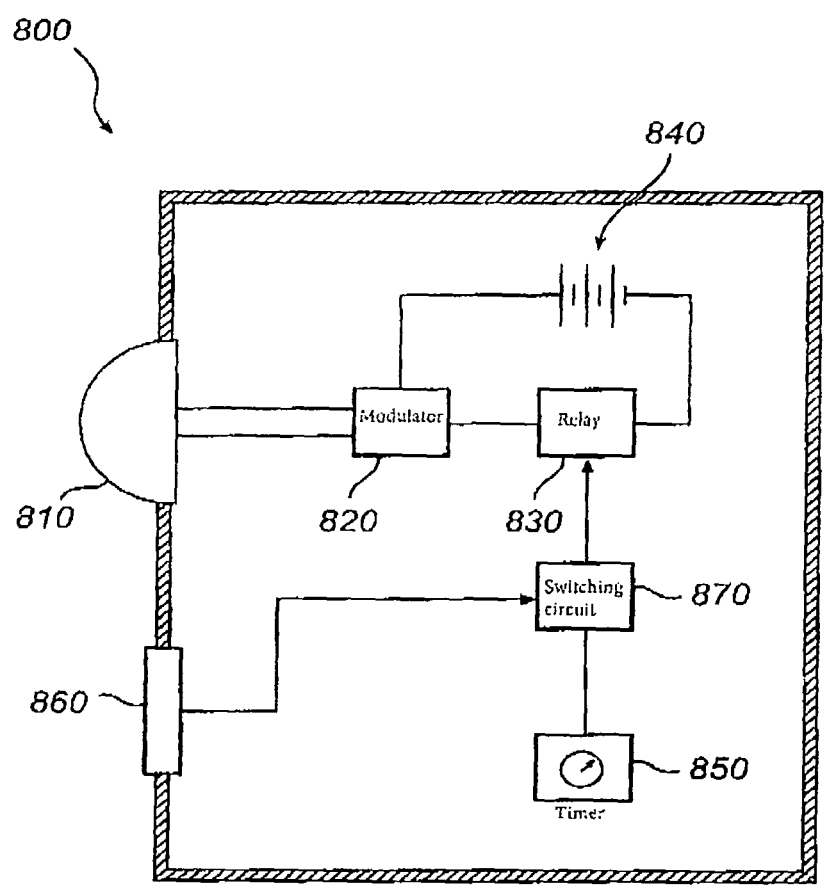
FIG. 8 shows an IR signal source for use in a system for detecting a gaze point of at least one person, in accordance with an embodiment of the present invention.

FIG. 8 is a diagrammatic drawing of an IR signal source 800 in accordance with an embodiment of the invention. The source 800 has an IR light source 810 adapted to emit time-modulated IR light and a receiver 860 adapted to receive a wireless activation signal from an activation signal transmitter arranged in the eye glasses of the system. Optionally, further modulation can be achieved by arranging a chromatic or polarising filter at the aperture of the light source 810. A modulator 820 provides the driving voltage to the light source 810, and is itself supplied by a voltage source 840. It is beneficial to the adaptability of the system to use a rechargeable battery as a voltage source. A relay 830 is serially connected to the voltage source 840 and the modulator 820 and is thereby operable to activate and deactivate the modulator 820. The relay 830 can be actuated by a signal from a switching circuit 870. The value of the switching circuit's 870 signal for controlling the switching circuit 840 is based on data provided by the receiver 860 and by a timer 850. For instance, the switching circuit 870 may be configured to cause the relay 830 to close the circuit supplying the light source 810 for a predetermined time interval (such as 5 minutes, which may be the expected duration of a measurement session) following each receipt of an activation signal. After the end of this time interval, the IR signal source 800 enters a power-saving mode. It is advantageous to use a completely passive receiver 860, so that the IR signal source 800 does not dissipate any energy during its latency before an activation signal is received.

Figure 10A:
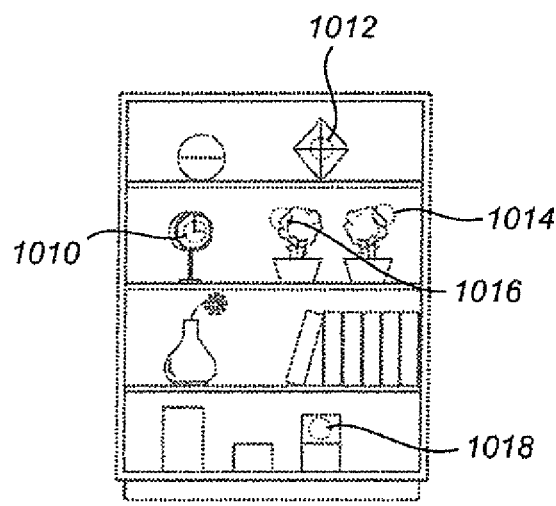
FIG. 10a is a combined picture of a region of space including indications of gaze points of a plurality of test subjects.
Figure 10B:
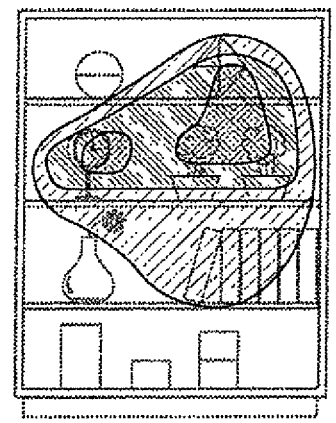
FIG. 10b is the combined picture of FIG. 10a, including indications of a statistical quantity as a function of position.
Figure 11:
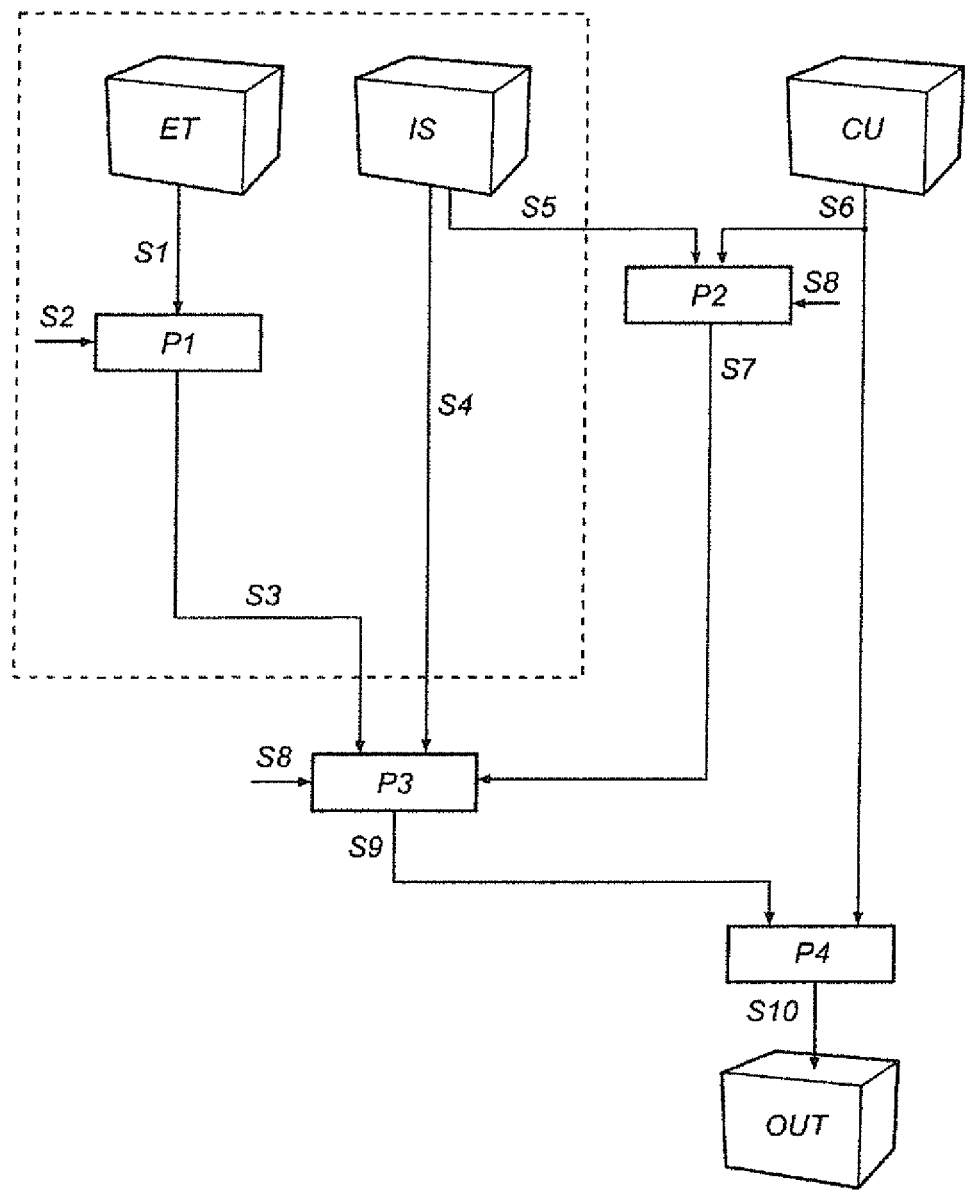
FIG. 11 is a flow chart showing how information is collected, processed and transmitted between different physical or functional components, in accordance with an embodiment of the inventive method for detecting a gaze point of at least one person with the assistance of optical reference signals.

With reference to FIGS. 9-12, the function of the gaze-point detection system will now be discussed. Firstly, FIG. 11 is a flowchart illustrating how the collected data are processed during operation of an embodiment of the invention. An eye-tracking unit ET has a detector which outputs an eye-tracking signal S1. An IR sensor IS receives IR signals from IR signal sources of the system and outputs an IR signal source tracking signal S4, which encodes the locations of the IR signal sources as seen from the IR sensor. Because the IR signal source tracking signal will be used for relating the eye-tracking signal S1 to a particular coordinate system, these signals are based on measurements that are simultaneous or approximately so. In the depicted exemplary embodiment, information concerning the location of the pupil and of the corneal reflection(s) (glint(s)) of the IR light source of the eye-tracking unit can be derived from the eye-tracking signal S1. In a first processing step P1, the eye-tracking signal is combined with personal calibration data S2 and a gaze point S3 is obtained. As used in this context, personal calibration data S2 may include:

horizontal and vertical angles between visual and optical axes of the eye, radius of corneal curvature, and distance between the centre of the pupil and the centre of corneal curvature.

Computational methods for determining the gaze direction (and thus the gaze point in an image plane) on the basis of an eye image containing at least one corneal glint are known in the art, e.g., through the teachings of E. D. Guestrin and M. Eizenmann in *IEEE Transactions on Biomedical Engineering*, Vol. 53, No. 6, pp. 1124-1133 (June 2006), which is included herein by reference.

The steps having been described in the preceding paragraph (which are symbolically represented inside the dashed rectangle in FIG. 11) are to be performed once for each test subject. What will now be discussed is directed to the final processing and presentation of the data, which may, in this embodiment, be performed on the data stream continuously or, in case the data are stored temporarily, at an arbitrary later point in time. Storing the eye-tracking signal S1 temporarily and performing the processing into gaze-point data S3 in connection with the final processing steps appear to be an equivalent choice. Still, the data volume of the eye-tracking signal S1, which may be represented as a video sequence of IR images of the eye, is much larger than that of the gaze-point data S3, so the use of the first processing step P1 as a pre-processing step may in fact be influential to the performance of the system. As an alternative to performing the first processing step P1 prior to temporary storage, the images encoded in the eye-tracking signal S1 may be cropped, filtered and/or compressed to save space and/or bandwidth.

With reference again to FIG. 11, the IR sensor and the camera unit CU (which is of course functionally equivalent to, and will not be distinguished in this disclosure from, an external scene camera) respectively acquire an IR signal source tracking signal S5 and a picture S6 (snapshot) of the test scene at an arbitrary point in time. In a second processing step P2—which uses hardware calibration data S8 relating the reference frames of the camera unit CU and the IR sensor IS—the picture S6 of the test scene and the corresponding IR signal source tracking signal S5 are compared in order that a relationship S7 between the IR signal source locations and the picture elements of the test scene picture is obtained. To illustrate, FIG. 9a shows a picture of an exemplary test scene (the bookcase 220 of FIG. 2) in which the locations 910 of the IR signal sources have been visualised as double circles. Thus, the four locations 910 correspond to four definite picture elements of the test scene picture S6; identifiers (coordinates) of these picture elements may be used to encode the relationship S7. A third processing step P3 has as its input variables the simultaneously acquired gaze point data S3 and the IR signal source tracking signal S4. Further, parameters necessary for the computations are derived from the hardware calibration data S8 and the relationship S7 between the IR signal source locations and the test scene picture. This third processing step P3 consists in a transformation of the gaze point S3 from a moving reference frame of the eye-tracking unit into a reference frame of the test scene picture S6. In this embodiment, the reference frame in the test scene picture is simply the picture elements. Hence, the gaze-point is expressed as gaze point picture elements S9. In a fourth processing step P4, the gaze point picture elements S9 are drawn (superimposed) on the picture S6 of the test scene, thereby yielding data S10 representing a combined picture, which are provided to an output means OUT, such as a monitor, a printer, an output file or an electronic message. An exemplary combined picture is shown in FIG. 9c, the gaze point being indicated by a dashed circle 930.

Figure 13:
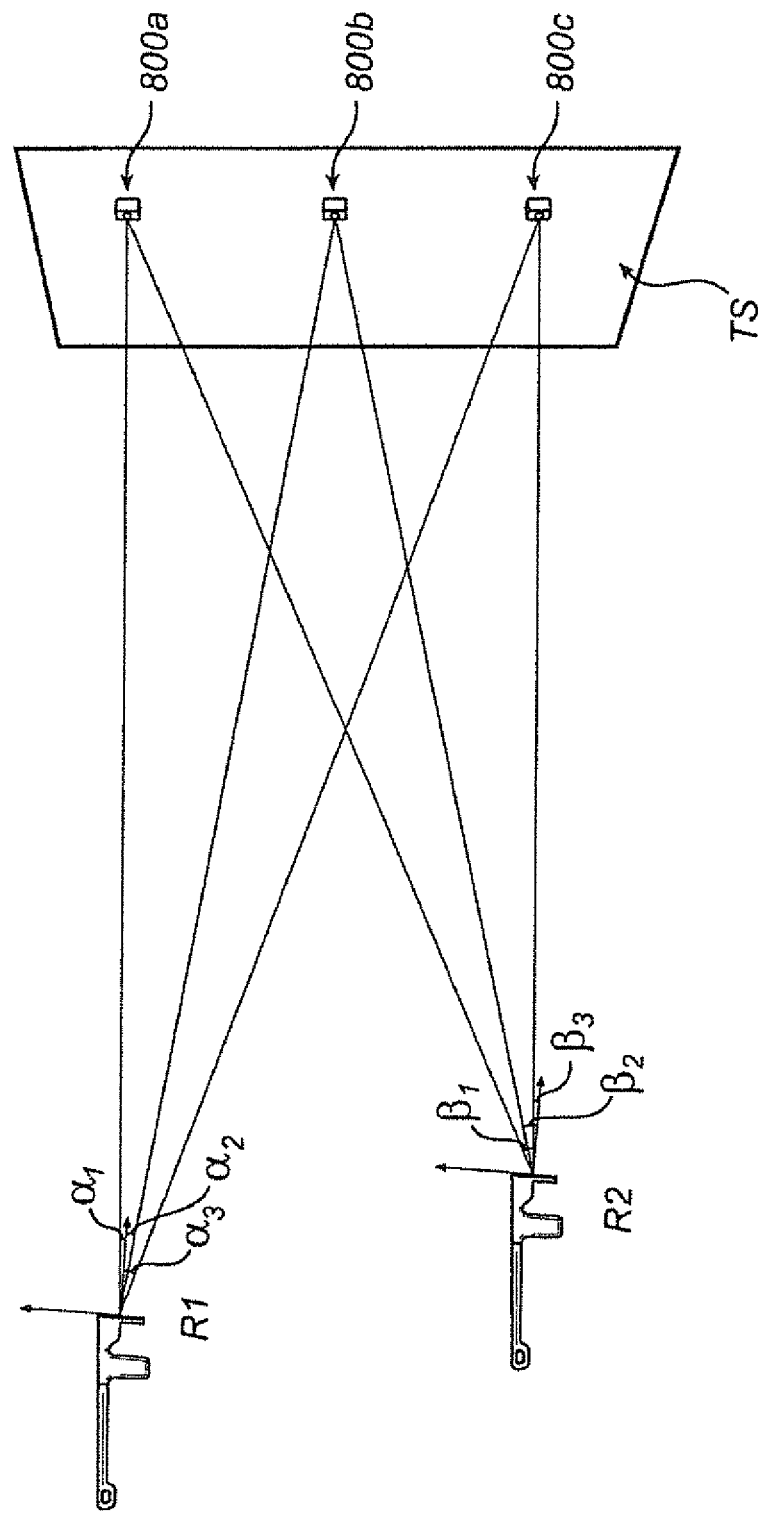
FIG. 13 is a simplified (in so far as all items are coplanar) drawing which shows two sets of angles corresponding to the lines of sight to three IR signal sources, as measured from two different positions of a pair of eye glasses.

The transformation of the gaze point, which is performed in the third processing step P3, more precisely is a perspective projection. As those skilled in the art will appreciate, a perspective projection of a point can be expressed as a linear mapping if the point is given in homogeneous coordinates. The perspective projection is the identity mapping if the eye glasses have not been dislocated. If instead the eye glasses have been moved (translated and/or rotated), then the perspective projection can be defined as the mapping which transforms the visual percept (image-plane points) of the IR signal sources at that point in time when the eye-tracking data S1 were collected into the visual percept of the IR signal sources when the test scene picture S6 was acquired. FIG. 13 shows an example of how angles-of-sight to three IR signal sources 800 in the test scene TS change, from a first triplet $(\alpha_1, \alpha_2, \alpha_3)$ into a second triplet $(\beta_1, \beta_2, \beta_3)$, when the eye glasses are displaced from a first position R1 to a second position R2. FIG. 13 is simplified in so far as the eye glasses are oriented identically in both positions and all objects in the figure are coplanar; in reality, two angles to each IR signal source are measured. In this embodiment, movements of the eye glasses are not traced, so that a priori, the perspective projection is only implicitly known. Preferably, the mapping is estimated on the basis of the IR signal source tracking signal S4 and the relationship S7 between the IR signal source locations and the test scene picture (the picture elements corresponding to the IR signal sources). The estimation may be effectuated by means of a direct linear transformation. As the skilled person will appreciate, a complete estimation of the perspective projection requires knowledge of at least four distinct IR signal source locations. The estimation will provide multiple solutions if fewer IR signal source locations are known. If the test scene picture S6 contains more than four IR signal sources, it may be advantageous to not use the excess ones. In particular, unwanted IR signals may appear in the test scene view as reflections or may emanate from sources behind the test scene. The selection of what IR signal sources to use may either be performed by a user or take place automatically in the system; e.g., the four most intensive IR signals may be selected as a part of the second processing step P2.

The precise distribution of the processing steps between different constituent parts of the system has not been discussed above. Storing and processing data are activities that gradually require less energy and occupy less physical space as the technological development progresses. The tasks can in fact be allocated in many, fairly equivalent ways. As an example, the allocation shown in table 1 may be applied.

TABLE 1

| Allocation of processing tasks | |
| --- | --- |
| Unit | Processing step(s) |
| Eye glasses | — |
| Support unit | P1, P2 |
| IR signal source | — |
| Data processing and storage unit | P3, P4 |

The distribution shown in table 1 may not be optimal if the following assumptions are true: (i) communication links between the eye glasses and their respective support units are slow and unreliable, as are communication links between the support units and the central data processing and storage unit; and (ii) numerical computations can be executed at the eye glasses at low battery consumption. In such conditions, the alternative allocation scheme set forth in table 2 may perform better.

TABLE 2

| Alternative allocation of processing tasks | |
| --- | --- |
| Unit | Processing step(s) |
| Eye glasses | P1, P2 |
| Support unit | P3 |
| IR signal source | — |
| Data processing and storage unit | P4 |

By routine experimentation, the skilled person will find a suitable distribution of the processing steps in a given situation once this specification has been read and understood.

Figure 12:
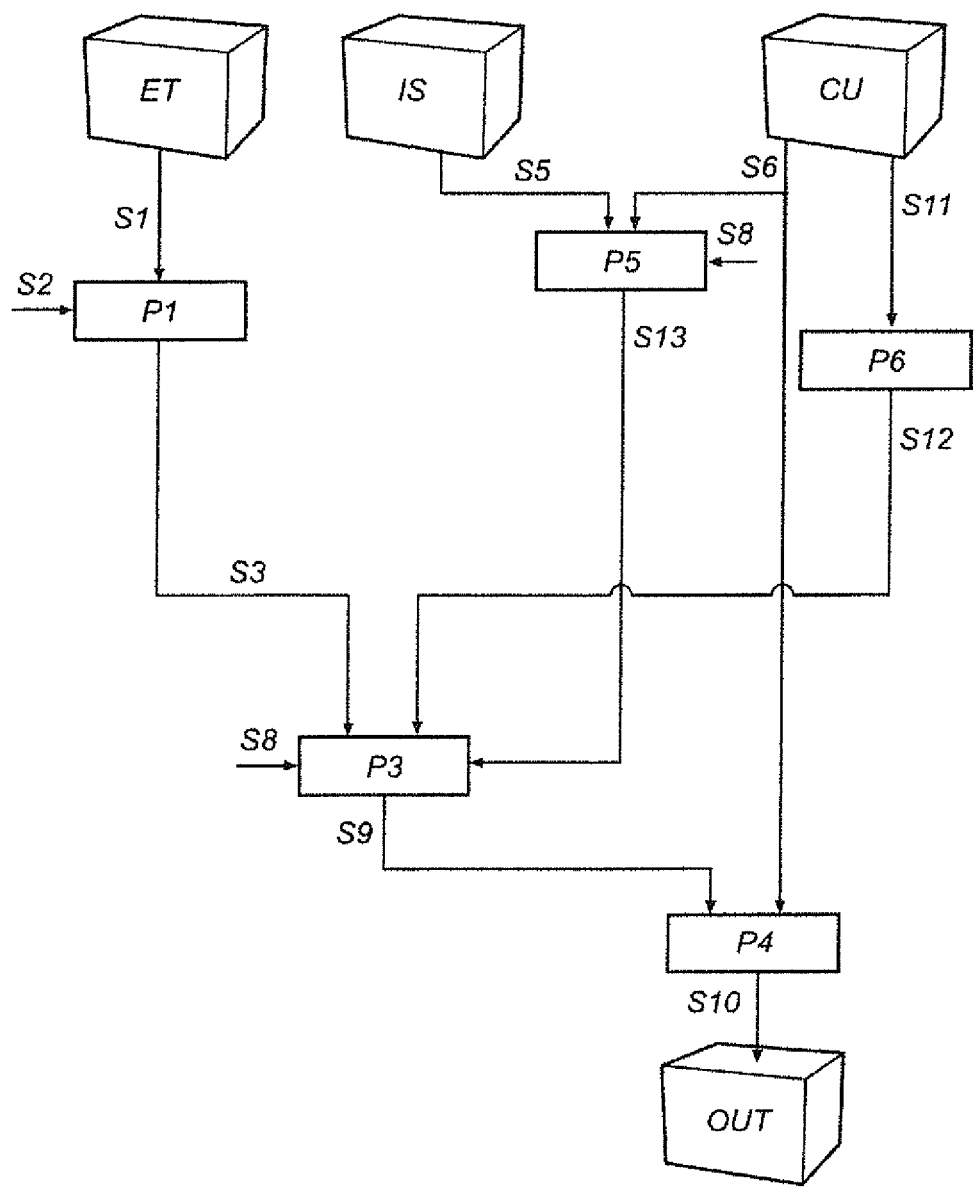
FIG. 12 is a flow chart of an alternative embodiment of the process shown in FIG. 11.

FIG. 12 illustrates an alternative embodiment of the process shown in FIG. 11. Advantageously, this embodiment is not dependent on the IR sensor IS receiving signals from all IR signal sources at every instant that an eye-tracking signal is generated. To compensate for one or more lost IR signals, it is required that the camera unit CU has acquired a picture of the test scene when the eye-tracking signal was generated. As a simplified example, it is assumed that an eye-tracking signal S1 and a test scene picture S11—but no IR signal—were received at one point in time. Prior to this point in time, a complete set of IR signal sources S5 have been received and located in the test scene picture S6, like in the second processing step P2 in the embodiment described above. Additionally in this alternative embodiment, image features are extracted from the picture and located and stored for later use. The locating of IR signal sources and of extracted image features, the totality of which is denoted by S13, is effectuated in an alternative second processing step P5. The output S13 can be visualised as in FIG. 9b, wherein the previously shown IR signal source locations 910 are complemented by image feature locations 920. In FIG. 9b, the following image features have been extracted: a top corner 920a of the octahedron, a support 920b of the clock, a top left corner 920c of the leftmost book, and an intersection point 920d of various structural elements of the bookcase 220. It is assumed that these four image features have been extracted and located in both the test scene picture S6 and in a more recent test scene picture S11, namely one having been acquired simultaneously with the eye-tracking signal S1. The extraction of image features S12 from the test scene picture S11 is done in an extraction step P6 to be performed before the third processing step P3. In the third processing step P3, which includes estimating the perspective projection which compensates possible eye glass movements, the positions of the image features are used as inputs to the estimation algorithm. Hence, to resolve a possible ambiguity of the solutions of the perspective projection estimation problem, the extracted image features take the role of the IR signal sources in case one or more of the latter are lost. The fourth processing step P4 is performed as in the embodiment described above. It is noted that IR signals sources are in some respects superior to extracted image features in the role as reference points. The location of an image feature may be difficult to establish with good accuracy; tracking the feature when the viewing angle of the test scene changes may prove delicate; and most importantly, the attention of the test subject may be distracted by image features, which are, unlike IR light, visible. For these reasons, image features should be viewed merely as a supplement to the IR signal sources.

As an alternative to feature tracking, Kalman filtering can be used for reconstructing the position of the eye glasses in cases where the set of received IR signals is incomplete. A Kalman filter for position and orientation estimation based on optical reference signals is disclosed in G. F. Welch, *SCAAT: Incremental tracking with incomplete information*, doctoral thesis, University of North Carolina, Chapel Hill (October 1996), which is included herein by reference. The IR signal source tracking history is then used in association with assumptions on, e.g., the maximal acceleration of persons wearing the eye glasses of the system. In a simpler approach, one may alternatively use the latest estimated perspective projection as an initial guess; apart from accelerating the estimation, this may also prevent the estimation algorithm from converging to a false solution. As yet another alternative, if a history of observations is available around the point in time having incomplete data (this implies that the processing is accomplished non-causally), linear interpolation between two known points may be used.

The presentation of gaze-point data detected by a system according to the invention can be fashioned in a multitude of formats. As an example, FIG. 10a is a combined test scene picture with gaze points shown as dashed circles 1010, 1012, 1014, 1016, 1018. The circles 1010, 1012, 1014, 1016, 1018 may correspond to momentary gaze points of different test subjects ('bee swarm' view). They may also correspond to gaze points of one test subject at different points in time ('gaze plot' view), provided the gaze-point detection covers a time interval of non-zero length. In this case, the circles 1010, 1012, 1014, 1016, 1018 may be complemented by textual annotations to specify their respective time of viewing; they may also be connected by lines or arrows to show the order of viewing, that is, the path of the viewer's gaze. Dots, stars, rectangles, crosses or other shapes may be used in the place of circles, as deemed appropriate in each application. The size of each shape may be indicative of the accuracy of the detection, in that a larger shape may correspond to a greater numeric uncertainty, FIG. 10b is a test scene picture having superimposed shaded regions ('heat map' view). Here, a deeper colour corresponds to a longer dwelling time of the gaze. Such dwelling time can have been accumulated over a test session including only one test subject or may be the sum of dwelling times of a plurality of test subjects. According to an alternative data presentation method, a plurality of areas of interest are predefined and the dwelling time in each is accumulated during a test session including one or more test subjects. The respective areas of interest are shaded in accordance with statistical measures of the dwelling times and are superimposed on a test scene picture ('cluster view'). Statistical measures include: mean total dwelling time per test subject, mean duration of each fixation, percentiles of the total dwelling time, percentiles of the test subject population having visited each area of interest, etc.

In a particular embodiment, test scene pictures are acquired at regular time intervals (such as 10-100 pictures per second and suitably 20-40 pictures per second) by the camera unit of the eye glasses. This way, a video sequence of the test scene is obtained. The gaze point may then be represented by superimposed graphical symbols, not on a stationary test scene picture but on respective frames of the video sequence of the test scene. (It is noted that even when only one test scene picture is acquired, the frames in such a video sequence could in principle be reconstructed on the basis of IR signal source tracking data by applying perspective transformations to the one test scene picture; the associated computational effort would be comparatively large.) This embodiment may be particularly useful in connection with simulators. It is also advantageous in studies where the test scene is a video monitor presenting a variable visual stimulus to the test subject. Indeed, a comprehensive evaluation of the results, in terms of the gaze point at different points in time, should take into account what image the test subject has been presented with at a given moment.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure and the appended claims. In the claims, the word 'comprising' does not exclude other elements or steps, and the indefinite article 'a' or 'an' does not exclude a plurality. The mere fact that certain features are recited in mutually different dependent claims does not indicate that a combination of these features cannot be used to advantage. Any reference signs in the claims should not be construed as limiting the scope.

The invention claimed is:

1. A system for presenting gaze-point data comprising: an eye tracking unit for detecting gaze point data of at least one subject; a camera unit for viewing a test scene and acquiring a picture representing the test scene; a display; a processing unit configured to present the picture on said display, and display shapes on the picture with the shapes representing momentary gaze points, detected by said eye-tracking unit, of the at least one subject, with a size of each shape varying to indicate accuracy of the gaze-point data; said eye-tracking unit to acquire momentary gaze points over a time interval of non-zero length; and said processing unit is further configured to display textual annotations specifying a respective time of viewing of the momentary gaze points, display lines or arrows connecting the shapes to specify an order of the momentary gaze points, accumulate the dwell time of one or more subjects in each area of interest, and superimpose shaded areas of interest in accordance with statistical measures of the dwell times of the one or more subjects, with the statistical measures comprising at least one of a mean total dwell time per test subject, a mean duration of each fixation, percentiles of the total dwell time or percentiles of a test population having visited each area of interest.

2. The system of claim 1, wherein the shapes comprise at least one of circles, dots, stars, rectangles and crosses.

3. A system for presenting gaze-point data comprising:
an eye tracking unit for detecting gaze point data of at least one subject;
a camera unit for viewing a test scene and acquiring a picture representing the test scene;
a display; and
a processing unit configured to:
  present the picture on the display, and
  display shapes on the picture with the shapes representing momentary gaze points, detected by said eye-tracking unit, of the at least one subject, with a size of each shape varying to indicate accuracy of the gaze-point data;
said eye-tracking unit to acquire momentary gaze points over a time interval of non-zero length, with a color of the shapes indicating a dwell time of the at least one subject's gaze.

4. The system of claim 3, wherein the shapes represent a sum of dwell times of a plurality of subjects.

5. A system for presenting gaze-point data comprising: an eye tracking unit for detecting gaze point data of at least one subject; a camera unit for viewing a test scene and acquiring a picture representing the test scene; a display; a processing unit configured to present the picture on the display, and display shapes on the picture with the shapes representing momentary gaze points, detected by said eye-tracking unit, of the at least one subject, with a size of each shape varying to indicate accuracy of the gaze-point data; said eye-tracking unit to acquire momentary gaze points over a time interval of non-zero length; and said processing unit is further configured to predefine a plurality of areas of interest in the test scene picture, display lines or arrows connecting the shapes to specify an order of the momentary gaze points, accumulate the dwell time of one or more subjects in each area of interest, and superimpose shaded areas of interest in accordance with statistical measures of the dwell times of the one or more subjects, with the statistical measures comprising at least one of a mean total dwell time per test subject, a mean duration of each fixation, percentiles of the total dwell time or percentiles of a test population having visited each area of interest.

6. The system of claim 5, wherein said processing unit is further configured to construct a video sequence based on the test scene picture in combination with an IR signal source tracking data provided by said eye tracking unit by applying perspective transformations.

7. The system of claim 5, wherein said processing unit is further configured to present a plurality of test scene pictures acquired at regular intervals forming a video sequence, and display shapes on respective frames of the video sequence.

* * * * *